United States Patent
Kariathungal et al.

(10) Patent No.: US 7,860,285 B2
(45) Date of Patent: Dec. 28, 2010

(54) RADIOLOGICAL IMAGING OF PATIENT FUNCTIONAL UNITS

(75) Inventors: Murali Kumaran Kariathungal, Hoffman Estates, IL (US); Prakash Mahesh, Hoffman Estates, IL (US); Mark M. Morita, Arlington Heights, IL (US)

(73) Assignee: General Electric Company, Schenectady, NY (US)

( * ) Notice: Subject to any disclaimer, the term of this patent is extended or adjusted under 35 U.S.C. 154(b) by 938 days.

(21) Appl. No.: 11/696,022

(22) Filed: Apr. 3, 2007

(65) Prior Publication Data

US 2008/0247617 A1 Oct. 9, 2008

(51) Int. Cl.
*G06K 9/00* (2006.01)
*G01N 23/04* (2006.01)

(52) U.S. Cl. .......................................... 382/128; 378/62

(58) Field of Classification Search .................. 382/128, 382/129, 130, 131, 132, 133, 134, 173; 128/915, 128/916, 920, 922; 600/407, 410, 425; 378/4, 378/8, 21–27, 101, 901
See application file for complete search history.

(56) References Cited

U.S. PATENT DOCUMENTS

| 5,740,267 A | * | 4/1998 | Echerer et al. .............. 382/132 |
| 6,950,492 B2 | * | 9/2005 | Besson .......................... 378/5 |
| 2006/0058699 A1 | * | 3/2006 | Vitiello et al. .............. 600/546 |

\* cited by examiner

*Primary Examiner*—Abolfazl Tabatabai
(74) *Attorney, Agent, or Firm*—McAndrews, Held & Malloy, Ltd.; Michael A. Dellapenna

(57) ABSTRACT

Certain embodiments provide a method for radiological imaging including: receiving a set of image data, the image data further including information corresponding to at least one functional portion of a patient; identifying the information corresponding to the at least one functional portion of the patient; and grouping the information corresponding to the at least one functional portion of the patient into a group. In an embodiment, the method is performable substantially automatically. In an embodiment, the method further includes enhancing at least a portion of the group. In an embodiment, the enhancing at least a portion of the group is performable automatically. In an embodiment, the enhancing at least a portion of the group is performable manually. In an embodiment, the enhancing at least a portion of the group includes at least one of: applying a look up table; applying a window level; applying an algorithm; and applying a filter.

20 Claims, 4 Drawing Sheets

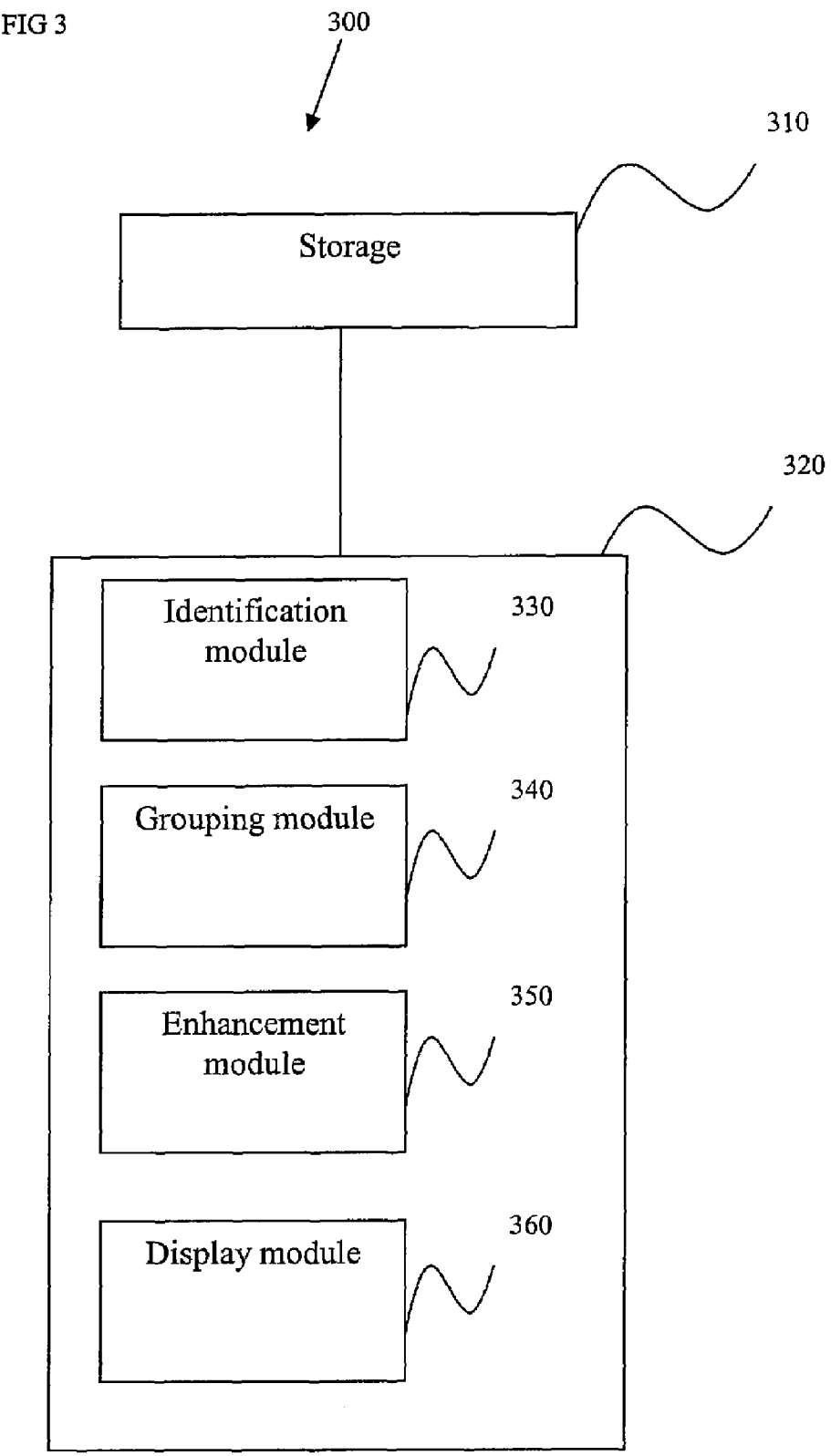

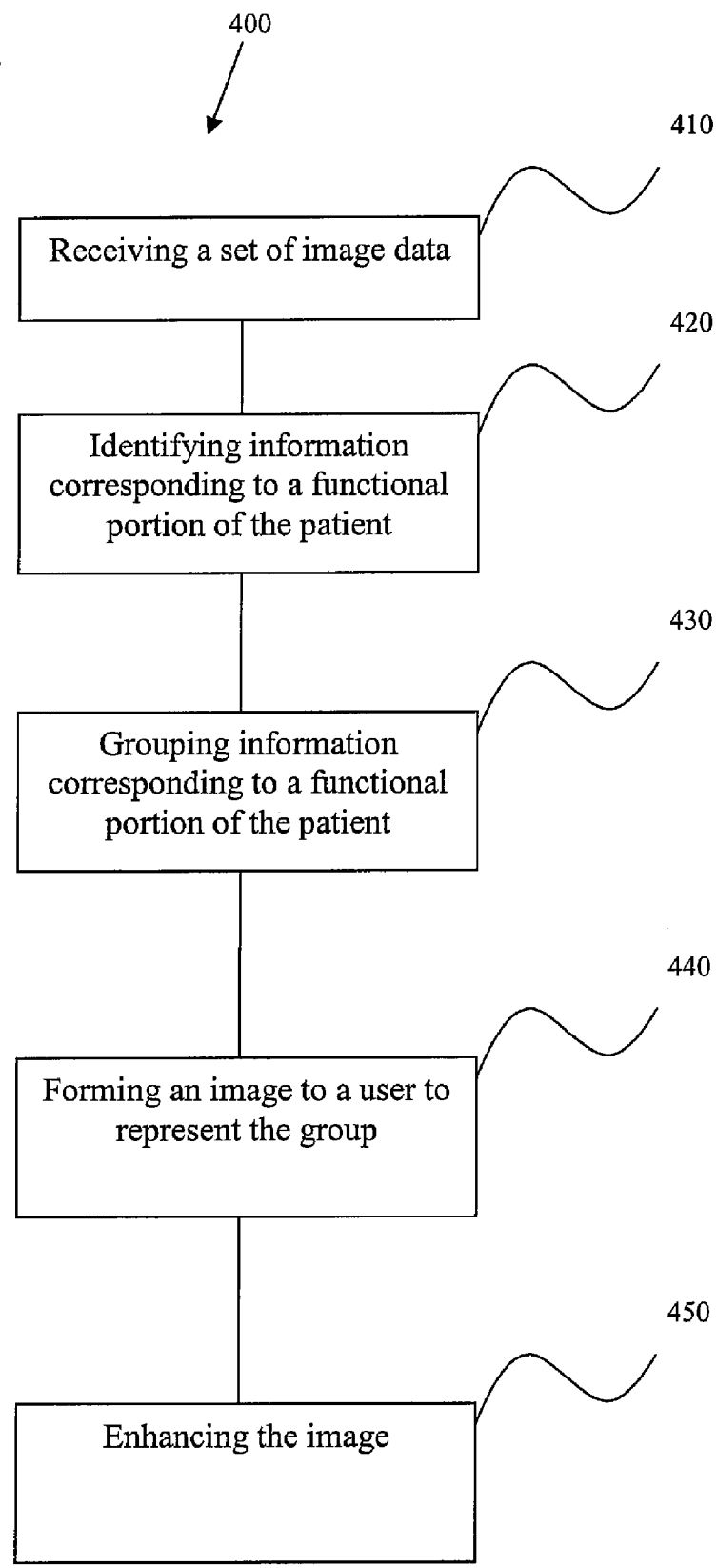

ively. In an embodiment, the enhancing at least a portion of the group is performable manually. In an embodiment, the enhancing at least a portion of the group includes at least one of: applying a look up table; applying a window level; applying an algorithm; and applying a filter. In an embodiment, the at least one functional portion of the patient includes at least one of: an organ; a tissue; a bone; and a vessel. In an embodiment, the method further includes displaying at least a portion of the functional unit to a user. In an embodiment, the at least one functional portion spans across at least two body parts.

RADIOLOGICAL IMAGING OF PATIENT FUNCTIONAL UNITS

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

Embodiments of the present application relate generally to systems and methods for radiological imaging. Particularly, certain embodiments relate to techniques for grouping radiological image data based on functional portions of a patient.

Radiological clinicians (e.g., radiologists) routinely review large quantities of image data. It may be possible so simplify the reading of a radiological study by grouping images based on the body part. A body part may, for example, refer to the physical location or area of a patient's anatomy. A body part may consist of multiple organs or tissue types. Examples of body parts include chest, abdomen, pelvis, head, neck, and/or the like.

FIG. 1 illustrates how images may be grouped by body part. A radiological image 100 includes various organs, tissues, and body parts. Two body parts are shown—chest 102, and abdomen 104. Body parts may contain different types of functional units, which might not be considered while grouping images.

In a radiology reading the images of a study may be grouped based on the body part and procedure, for example. A scan of a body part's images may be grouped together for a radiology reading as a single group or multiple image groups depending on grouping criteria. Furthermore, image enhancement techniques (e.g., window level and look tables) may be configured to correspond to the imaged body part and/or the procedure.

However, grouping by body part may not assist the clinician to efficiently navigate a study to focus on a specific functional unit of a patient. For example, as shown in FIG. 1, the chest 102 includes several organs, including the heart and lungs. Similarly, the abdomen 104 includes several organs, including the spine, and lungs, heart, and/or the like.

Instead of focusing on a body part, a clinician may wish to focus on a functional portion of a patient. A functional portion of a patient may be a portion of a functional unit, or may be a functional unit, for example. A functional unit is a portion of a patient that has particular clinical significance. A functional unit may include an organ, a tissue, a bone, a collection of organs, a collection of tissues, a collection of bones, and the like. A chest, abdomen CT study contains functional units such as heart, lungs, stomach, colon, and/or the like, for example. A slice from the study may contain pixels of different functional units. For example lung and heart may overlap in few of the image slices. While there are numerous examples of functional units, a few include a patient's heart, lung, or spine. Thus, a radiologist wishing to focus on a specific organ may not be able to efficiently navigate a study that is grouped by body parts.

In addition to grouping by functional portion, it may be useful to provide image enhancement that corresponds to the functional unit and/or procedure to assist a clinician to efficiently navigate and read a study.

Thus, there is a need for methods and systems that group study images according to functional portion(s) of a patient. There is a need for methods and systems that improve the efficiency of study navigation for clinicians focusing on functional portion(s). Additionally, there is a need for methods and systems that provide image enhancement corresponding to a functional unit of a patient.

BRIEF SUMMARY OF THE INVENTION

Certain embodiments provide a method for radiological imaging including: receiving a set of image data, the image data further including information corresponding to at least one functional portion of a patient; identifying the information corresponding to the at least one functional portion of the patient; and grouping the information corresponding to the at least one functional portion of the patient into a group. In an embodiment, the method is performable substantially automatically. In an embodiment, the method further includes enhancing at least a portion of the group. In an embodiment, the enhancing at least a portion of the group is performable automatically. In an embodiment, the enhancing at least a portion of the group is performable manually. In an embodiment, the enhancing at least a portion of the group includes at least one of: applying a look up table; applying a window level; applying an algorithm; and applying a filter. In an embodiment, the at least one functional portion of the patient includes at least one of: an organ; a tissue; a bone; and a vessel. In an embodiment, the method further includes displaying at least a portion of the functional unit to a user. In an embodiment, the at least one functional portion spans across at least two body parts.

Certain embodiments provide a system for radiological imaging including: a set of image data, the image data further including information corresponding to at least one functional portion of a patient; an identification module for identifying the information corresponding to the at least one functional portion of the patient; and a grouping module for grouping the information corresponding to the at least one functional portion of the patient into a group. In an embodiment, the identification module is capable of automatically identifying the information, and wherein the grouping subsystem is capable of automatically grouping the information. In an embodiment, the system further includes an image processing module capable of performing at least one of: applying a look up table; applying a window level; applying an algorithm; and applying a filter. In an embodiment, the functional portion of the patient includes at least one of: an organ; a tissue; a bone; and a vessel. In an embodiment, the system further includes a display module capable of displaying the functional portion of the patient to a user.

Certain embodiments provide a computer-readable storage medium including a set of instructions for a computer, the set of instructions including: a reception routine for receiving a set of image data, the image data further including information corresponding to at least one functional portion of a patient; an identification routine for identifying the information corresponding to the at least one functional portion of the patient; and a grouping routine for grouping the information corresponding to the at least one functional portion of the patient into a group. In an embodiment, the identification routine is capable of automatically identifying the information, and wherein the grouping routine is capable of automatically grouping the information. In an embodiment, the set of instructions further includes a processing routine for automatically processing at least a portion of the group. In an embodiment, the set of instructions further includes a processing routine for facilitating manual processing at least a portion of the group. In an embodiment, the formation routine is capable of automatically enhancing the image. In an embodiment, the processing routine is capable of at least one of: applying a look up table; applying a window level; and applying an algorithm; and applying a filter.

BRIEF DESCRIPTION OF SEVERAL VIEWS OF THE DRAWINGS

FIG. 3 shows a system for radiological imaging, according to embodiments of the present invention.

FIG. 4 shows a flowchart for radiological imaging, according to embodiments of the present invention.

Figure 1:
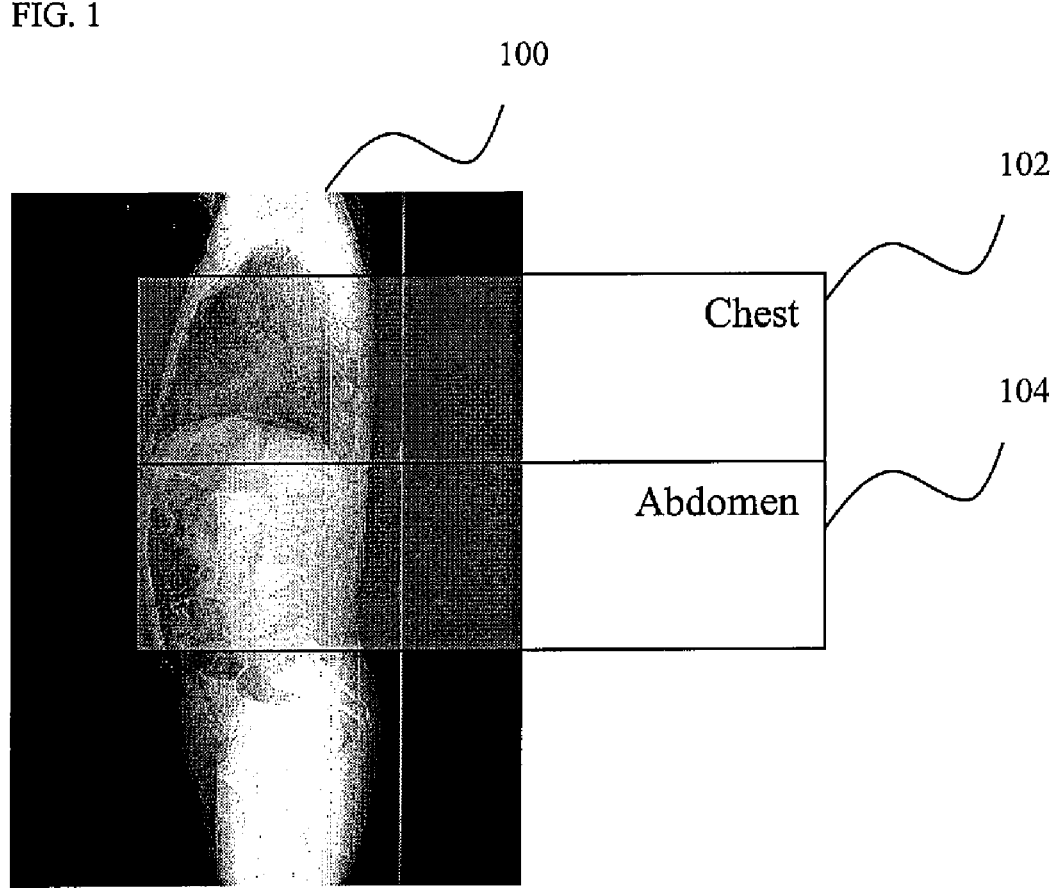
FIG. 1 shows a radiological image.

The foregoing summary, as well as the following detailed description of certain embodiments of the present application, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Figure 2:
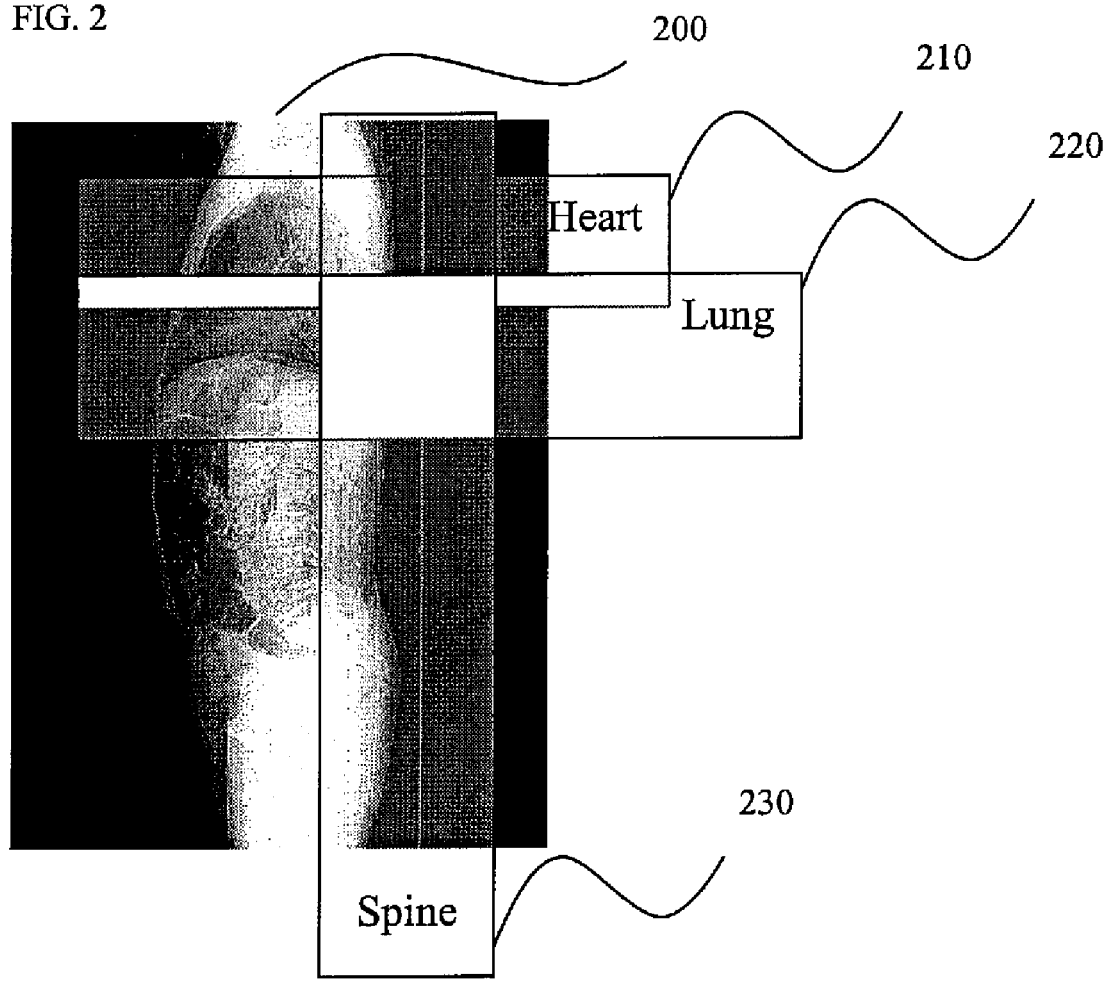
FIG. 2 shows a radiological image, according to embodiments of the present invention.

FIG. 2 shows a radiological image, according to embodiments of the present invention. A radiological image 200 includes one or more body part of a patient. A radiological image 200 may be a scout image (as shown), or any of a variety of other types of images, including sagittal, axial, coronal, three dimensional, four dimensional, and/or the like. A scout image may be constructed from axial images, for example. A radiological study may include one or more radiological images that correspond to a patient and/or a procedure, for example. Similar to radiological image 100, image 200 may include more than one body part—e.g., chest and abdomen.

A body part (e.g. 102, 104) may include one or more functional portions. Functional portions may span multiple images within a study and/or overlap with other functional portions, functional portions. Functional portions may span across multiple body parts, for example.

It may be possible for a clinician to read images having functional portions in the following manner, for example: (a) apply look up table or window level based on a functional portion and read the image; (b) apply other image processing functions (e.g., bone removal, and/or highlighting vessels) based on the functional portion of interest; and (c) repeat steps (a), and (b) for other functional portions of interest. Other possibilities exist, such as performing step (b) before step (a), or by performing steps (a) and (b) in parallel for each functional portion of interest.

FIG. 3 shows a system 300 for radiological imaging, according to embodiments of the present invention. The storage 310 may be any digital storage medium, such as hard disk, optical disk, magnetic disk, RAM, ROM, flash, and/or the like, for example. The storage 310 may be capable of storing electronically a set of image data, for example. A set of image data may include radiological images, such as a study, for example. A set of image data may also include associated information, such as patient identification, procedure identification, clinician identification, and/or the like, for example. The storage 310 may be integrated with processing subsystem 320, or may be physically separate. The storage 310 may communicate with the processing subsystem 320, for example, to transfer image data from the storage 310 to the processing subsystem 320.

A processing subsystem 320 may be an integrated device, such as a computer, or a collection of components. A processing subsystem 320 may be a PACS, for example. A processing subsystem 320 may interpret and execute set of instructions to run an application, routine, or subroutine, for example. The processing subsystem 320 may be capable of receiving a set of image data, for example, such as a set of image data from storage 310. A processing subsystem 320 may contain various modules, such as an identification module 330, a grouping module, 340, an enhancement module 350, and/or a display module 360, for example. Any given module may be a separate component that includes software and/or hardware, for example. Modules may be integrated with other modules, either completely or partially, for example. Modules may be software routines and/or applications. The modules may be capable of interaction with other modules. Modules may include a computer-readable storage medium that includes a set of instructions that facilitate the operations of the module. One or more computer-readable storage media may be storage 310 and/or may reside within processing subsystem 320, for example.

The identification module 330 may be capable of identifying information that corresponds to at least one functional portion of a patient. The type of functional portion to be identified may be determined in a variety of ways, for example, such as: automatically, based on data or metadata in the set of image data (e.g. procedure, purpose of procedure, physician notes, etc.); automatically, based on a user's preferences; or manually, by permitting a user to select the functional portion. The identification module 330 may be capable of recognizing the content of radiological image data. Based on the functional portion to be identified, the identification module 330 may recognize and identify portions of the image data that correspond to the functional portion to be identified.

The identification module 330 may identify functional portions in a series of images, from an imaging study (e.g., CT SCAN), for example. The identification module 330 may perform identification automatically, according to image recognition algorithms, for example. As an example, automatic identification may be performable by segmentation and/or classification to extract features from image data. Features may further be used along with pattern recognition to identify functional portions of a patient, for example. As another example, the identification module 330 may permit and/or facilitate a user to manually identify functional portion(s) of the image data. For example, the identification module 330 may permit and/or facilitate a user to employ a scout or reference image to identify the functional portion(s) of interest. As an illustrative example, the identification module 330 may recognize the user's interaction with an electronic scout image, and record the user's directives with respect to identifying the functional portion(s) of interest.

The identification module 330 may implement both manual and automatic techniques. For example, the identification module 330 may receive a user's directive for identification of a functional portion in a 2D scout image. Then, the identification module 330 may automatically identify corresponding functional portions in other images, such as a series of 2D images that form a 3D image, for example.

The identification module 330 may also be capable of identifying various sub-portions of a functional portion, for example. As an illustrative example, a spinal column includes a number of vertebrae, discs, and other tissue types. Identification module 330 may be able of identifying the various tissues and bones that make up a spinal column (or a portion thereof).

Furthermore, the identification module may be capable of identifying radiological image data that may not be clinically relevant for a given image. For example, the identification module may be capable of identifying organs, tissues and/or the like that may interfere with an efficient reading of the functional portion. For example, potentially interfering soft tissues and/or bones may be identified. Potentially interfering structures may also be identified/filtered by the enhancement module 350, as discussed below.

The grouping module 340 may be capable of grouping the identified portions of image data into a group that corresponds to the functional portion to be identified. Once the functional portion(s) and/or sub-portion(s) have been identified, the grouping module 340 may group the identified portion(s)/sub-portion(s) to form group(s) corresponding to the functional portion(s). For example, a number of sub-portions (e.g. vertebrae in a spinal column) may be identified by identification module 330, and then grouped into a functional portion spinal column by grouping module 340. Grouping module 340 may also be capable of grouping identified portions across a series of images, such as a study, for example. Grouping may be carried out, for example, according to automated techniques, clinician preference, and/or clinician directive.

The enhancement module 350 may be capable of enhancing a functional portion. For example, the enhancement module 350 may be capable of applying image enhancement techniques, such as applying a look-up table or window level to the functional portion. Other examples of image enhancement include the application of algorithm(s). For example, the enhancement module 350 may be capable of applying vessel analysis to show vessels, or applying bone removal analysis to remove certain bones (or portions thereof) from the images. Such techniques may be performed by application of algorithm(s) and/or filter(s), for example. Algorithm(s) and/or filter(s) may also be performed by the identification module 330, for example. The enhancement module 350 may also be capable, for example, of applying any of a range of image processing techniques, for example.

One or more algorithms may be capable of enhancing and/or identifying a functional portion, for example. An algorithm may assist and/or perform segmentation of a functional portion. An algorithm may also assist and/or perform identification of a portion that is not a functional portion. By identifying various portions in an image, such identified portions may be highlighted or obscured to facilitate clinical review of a functional portion, for example. An algorithm may assist in enhancement and/or identification of a functional portion based on techniques other than segmentation, for example.

One or more filters may be capable of enhancing and/or identifying a functional portion, for example. A filter may assist and/or perform segmentation of a functional portion. A filter may also assist and/or perform identification of a portion that is not a functional portion. By identifying various portions in an image, such identified portions may be highlighted or obscured to facilitate clinical review of a functional portion, for example. An algorithm may assist in enhancement and/or identification of a functional portion based on techniques other than segmentation, for example.

The enhancement module 350 may perform image enhancement based on any of a variety of criteria, such as, for example: the functional portion of interest; one or more tissue types in the functional portion; clinician preference; patient; and procedure. By enhancing the functional portion, it may be more efficient for a clinician to analyze image data, such as a study, for example.

The display module 360 may be capable of displaying a functional portion to a user, such as a clinician, for example. A display module 360 may be capable, for example, of providing an image signal to be provided to a monitor, for example. A display module 360 may include a monitor, or may consist of a monitor, for example. A display module 360 may allow interaction from a user, such as a touch screen monitor.

FIG. 4 shows a flowchart for a method 400 for grouping functional units in radiological images in accordance with embodiments of the present invention. The steps of method 400 may be performable, for example, by a PACS system, or a radiological imaging system. For example, method 400 may be performable by a system such as radiological imaging system 300, or a portion thereof. Furthermore, the steps of method 400 may be performable in a different order, or some steps may be omitted. For example, steps 440 and 450 may be omitted. As another example, steps may be performed in a different order according to design and/or clinical preferences. Method 400, or a portion thereof, may be performable by one or more processing units. Method 400, or a portion thereof, may be performable by software, hardware, and/or firmware. Method 400, or a portion thereof, may also be expressible through a set of instructions stored on one of more computer-readable storage media, such as RAM, ROM, EPROM, EEPROM, optical disk, magnetic disk, magnetic tape, and/or the like.

At step 410, a set of image data may be received. For example, a set of image data stored in a storage device may be received by an image processing system. Image data may include one or more body parts and/or functional portions, as well as associated metadata and/or clinical information, for example. At step 420, information corresponding to a functional portion of a patient may be identified. For example, information corresponding to a functional portion of a patient may be identified by an image processing system. For example, identification may be performable by an identification module. It may be possible to identify more than one functional portions, either in parallel or consecutively. Step 420 may be performed by manual and/or automatic techniques, for example. At step 430, information corresponding to a functional portion of a patient may be grouped. The resulting group, may, then, correspond to the functional portion of the patient. One or more functional portions may be grouped. The group may span across two or more body parts, for example. Portions of a radiological image that have been identified as being a functional portion may be grouped. Portions of a series of radiological images may be grouped, for example, into a 3D or 4D functional portion group. At step 440, an image may be formed to represent a group. For example, the group may be processed to form data that can be displayed on a display. At step 450, an image and/or group may be enhanced. For example, an image may be enhanced to differentiate between functional portions and the remainder of a radiological image (e.g. 2D, 3D, and/or 4D images).

As an illustrative example, method 400 may be performed in the following manner. At step 410, a set image data is received from storage 310 by image processing subsystem 320. The image data includes a radiological study of a patient's abdomen and chest. The study resulted from two radiological procedures—one to image the chest, and the other to image the abdomen. The study contains a series of 2D images that can be rendered into a 3D image. The set of image data includes additional information, including the body part, the procedure, the patient, and the radiologist who performed the procedure.

At step 420, a functional portion of the patient is identified from the set of image data. The identification is performed by identification module 330, which is a routine executed by subsystem 320. In this example, the functional portion is the patient's spine. Portions of the patients spine are identified in both the patient's chest and abdomen. The spinal portions (e.g., vertebrae, disks, and other tissues that form the spine) are identified in a series 2D image slices in the set of image data. The spinal portions are identified using an automatic technique that recognizes specific types of objects within a given image.

At step 430, the identified spinal portions from the 2D images, and from the chest and abdomen, are grouped into a group that contains the functional portion of interest—the patient's spinal column. Grouping is performed by grouping subsystem 340, which is a routine executed on subsystem 320.

At step 450, the spinal column group and the set of image data is enhanced based on the procedures and clinician preferences associated with the set of image data. Enhancement is performed by enhancement module 350, which is a routine executed on subsystem 320. The image data is enhanced to facilitate the reading radiologist to distinguish the spinal column from the other radiological image data in the set of data. Specifically, window level and look-up tables are applied to the identified tissues and organs that make up the spinal column.

At step 440, the enhanced image data is formed into image data that will be sent to a display, to display to the reading radiologist. The image forming is performed by display module 360, which is a routine executed on subsystem 320. A series of 2D images in the study are rendered into a 3D image. The rendered image includes the patient's chest, abdomen, spinal column, and other proximal organs and tissues. The rendered 3D image is then displayed to a radiologist who reads the study.

In an embodiment, system 300 includes a computer-readable medium, such as a hard disk, floppy disk, CD, CD-ROM, DVD, compact storage, flash memory and/or other memory. The medium may be in storage 310, or subsystem 320. The medium may include a set of instructions capable of execution by a computer or other processor. The functions in method 400 described above may be implemented, at least in part, as instructions on the computer-readable medium.

For example, the set of instructions may include a reception routine for receiving a set of image data corresponding to a functional portion of interest. The receiving routine may facilitate implementation of step 410, described above in conjunction with method 400. The receiving routine may facilitate other aspects of system 300 and method 400 described above, for example.

Additionally, the set of instructions may include an identification routine for identifying information corresponding to a functional portion of interest in the patient. The identification routine may be able to facilitate implementation of step 420 or other steps, for example. The identification routine may be included in identification module 330. The identification routine 330 may identify information based on automatic and/or manual techniques.

Additionally, the set of instructions may include a grouping routine for grouping information corresponding to the functional portion of the patient. The grouping routine may be able to facilitate implementation of step 430 or other steps, for example. The grouping routine may be included in grouping module 340, for example.

Furthermore, the set of instructions may include an enhancement routine that automatically or manually. The enhancement routine may automatically or manually enhance the set of image data. The enhancement routine may be performed by enhancement module 350, and may apply various enhancement techniquest, such as, for example, window level and look-up table. Enhancement may be performed manually, automatically, according to procedure, according to clinician preference, according to the functional unit of interest, and/or the like.

Thus, embodiments of the present application provide methods and systems that group study images according to functional units of a patient. Embodiments of the present application provide methods and systems that improve the efficiency of study navigation for clinicians focusing on a functional unit. Additionally, embodiments of the present application provide methods and systems that provide image enhancement corresponding to a functional unit of a patient.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. For example, features may be implemented with software, hardware, or a mix thereof. Therefore, it is intended that the invention not be limited to the particular embodiment disclosed, but that the invention will include all embodiments falling within the scope of the appended claims.

The invention claimed is:

1. A method for radiological imaging, the method comprising:
    receiving a series of two-dimensional radiological images that form a three-dimensional radiological image, wherein the three-dimensional radiological image includes a first body part, a second body part, and a functional portion, and wherein the functional portion spans across each of the at least two body parts;
    identifying a plurality of sub-portions in a corresponding plurality of the two-dimensional radiological images in each of the first body part and the second body part;
    grouping the plurality of sub-portions into the functional portion; and
    displaying on a display the functional portion,
    wherein image data corresponding to the first body part is generated from a first radiological procedure and wherein image data corresponding to the second body part is generated from a second radiological procedure.

2. The method of claim 1, wherein the first body part comprises a chest, the second body part comprises an abdomen, and the functional portion comprises a spinal column.

3. The method of claim 2, wherein at least some of the sub-portions comprise vertebrae and disks.

4. The method of claim 1, further comprising enhancing the functional portion by applying at least one of a look up table or a window level.

5. The method of claim 1, further comprising identifying a non-functional portion in the three-dimensional radiological image.

6. The method of claim 5, wherein the step of displaying on a display the functional portion further comprises obscuring the non-functional portion.

7. The method of claim 1, further comprising permitting a user to manually identify the functional portion.

8. A system of radiological imaging, the method comprising:
- a storage configured to store a series a series of two-dimensional radiological images that form a three-dimensional radiological image, wherein the three-dimensional radiological image includes a first body part, a second body part, and a functional portion, and wherein the functional portion spans across each of the at least two body parts;
- a processing subsystem configured to receive the series of two-dimensional radiological images from the storage and including:
  - an identification module configured to identify a plurality of sub-portions in a corresponding plurality of the two-dimensional radiological images in each of the first body part and the second body part;
  - a grouping module configured to group the plurality of sub-portions into the functional portion; and
  - a display module configured to cause the functional portion to be displayed,
- wherein image data corresponding to the first body part is generated from a first radiological procedure and wherein image data corresponding to the second body part is generated from a second radiological procedure.

9. The system of claim 8, wherein the first body part comprises a chest, the second body part comprises an abdomen, and the functional portion comprises a spinal column.

10. The method of claim 9, wherein at least some of the sub-portions comprise vertebrae and disks.

11. The method of claim 8, wherein the processing subsystem further comprises an enhancement module configured to enhance the functional portion by applying at least one of a look up table or a window level.

12. The method of claim 8, wherein the identification module is further configured to identify a non-functional portion in the three-dimensional radiological image.

13. The method of claim 12, wherein the display module is further configured to cause the non-functional portion to be obscured.

14. A non-transitory computer-readable storage medium including a set of instructions for a computer, the set of instructions comprising:
- a reception routine for receiving a series of two-dimensional radiological images that form a three-dimensional radiological image, wherein the three-dimensional radiological image includes a first body part, a second body part, and a functional portion, and wherein the functional portion spans across each of the at least two body parts;
- an identification routine for identifying a plurality of sub-portions in a corresponding plurality of the two-dimensional radiological images in each of the first body part and the second body part;
- a grouping routine for grouping the plurality of sub-portions into the functional portion; and
- a display routine for displaying on a display the functional portion,
- wherein image data corresponding to the first body part is generated from a first radiological procedure and wherein image data corresponding to the second body part is generated from a second radiological procedure.

15. The set of instructions of claim 14, wherein the first body part comprises a chest, the second body part comprises an abdomen, and the functional portion comprises a spinal column.

16. The set of instructions of claim 14, wherein at least some of the sub-portions comprise vertebrae and disks.

17. The set of instructions of claim 14, further comprising an enhancement routine for enhancing the functional portion by applying at least one of a look up table or a window level.

18. The set of instructions of claim 14, further comprising an identification routine for identifying a non-functional portion in the three-dimensional radiological image.

19. The set of instructions of claim 18, further comprising an obscuring routine for obscuring the non-functional portion.

20. The set of instructions of claim 14, further comprising a permission routine for permitting a user to manually identify the functional portion.

* * * * *